United States Patent [19]
Salai

[11] Patent Number: 5,047,049
[45] Date of Patent: Sep. 10, 1991

[54] SELF ORIENTING INSTRUMENT HANDLE

[76] Inventor: Diane L. Salai, 3809 Dunraven Rd., Richmond, Va. 23236

[21] Appl. No.: 614,691

[22] Filed: Nov. 15, 1990

Related U.S. Application Data

[63] Continuation of Ser. No. 356,761, May 24, 1989, abandoned.

[51] Int. Cl.5 .............................................. A61B 17/00
[52] U.S. Cl. ........................................ 606/205; 606/1;
606/138; 606/210; 606/211
[58] Field of Search ............... 606/205, 210, 211, 138,
606/157, 104, 1

[56] References Cited

U.S. PATENT DOCUMENTS

| | | | |
|---|---|---|---|
| 2,406,393 | 8/1946 | Neugass | 606/210 X |
| 2,887,110 | 5/1959 | Roeschmann | 606/138 |
| 3,278,107 | 11/1966 | Rygg | 606/211 X |
| 3,302,648 | 2/1967 | Nelson | 606/208 X |
| 3,738,366 | 6/1973 | Blomberg | 606/210 |
| 4,192,314 | 3/1980 | Curutchet | 606/208 |
| 4,478,221 | 10/1984 | Heiss | 606/210 X |
| 4,610,252 | 9/1986 | Catalano | 606/210 X |

*Primary Examiner*—Robert A. Hafer
*Assistant Examiner*—Brian E. Hanlon
*Attorney, Agent, or Firm*—Stephen B. Salai

[57] ABSTRACT

An improved hand held medical instrument having an instrument tip having a preferred orientation, and rotatable to at least one other orientation, the tip being attached to an instrument handle adapted to be held in the hand of the user, the handle having at least one substantially round body portion for facilitating rotation of the instrument, and an at least generally flat reference surface on the body portion, the reference surface engagable by the hand of the user for orienting the instrument in the preferred orientation, or as a reference point in facilitating rotation to another position.

12 Claims, 1 Drawing Sheet

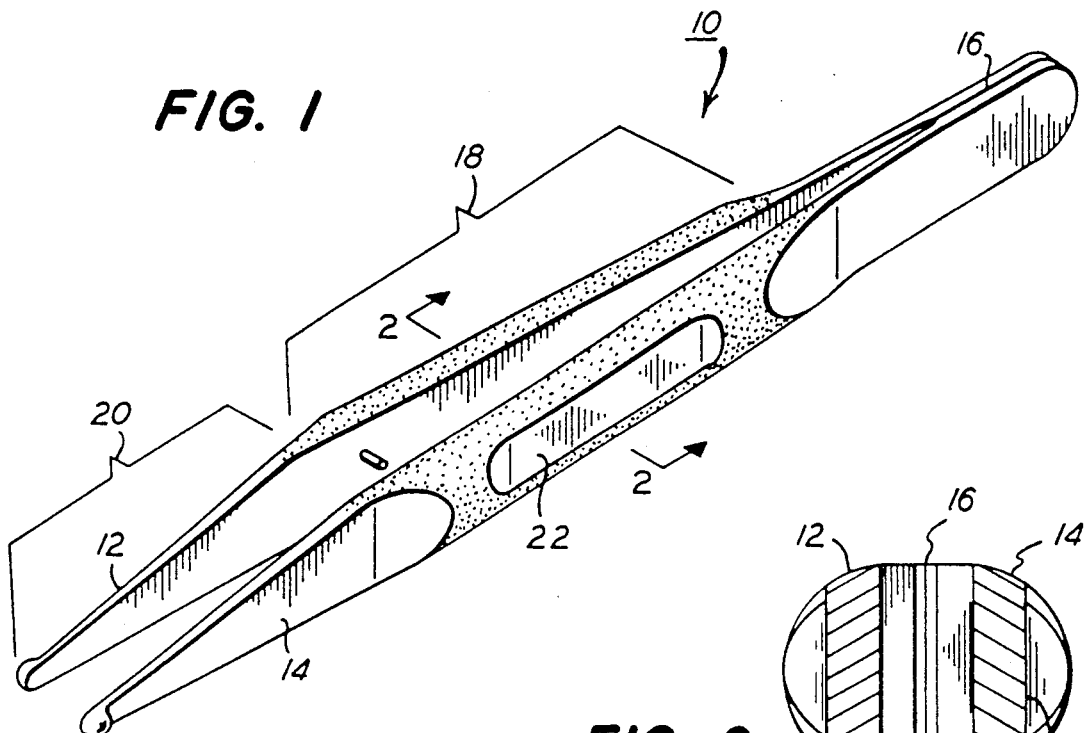
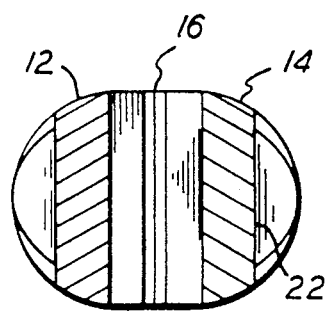
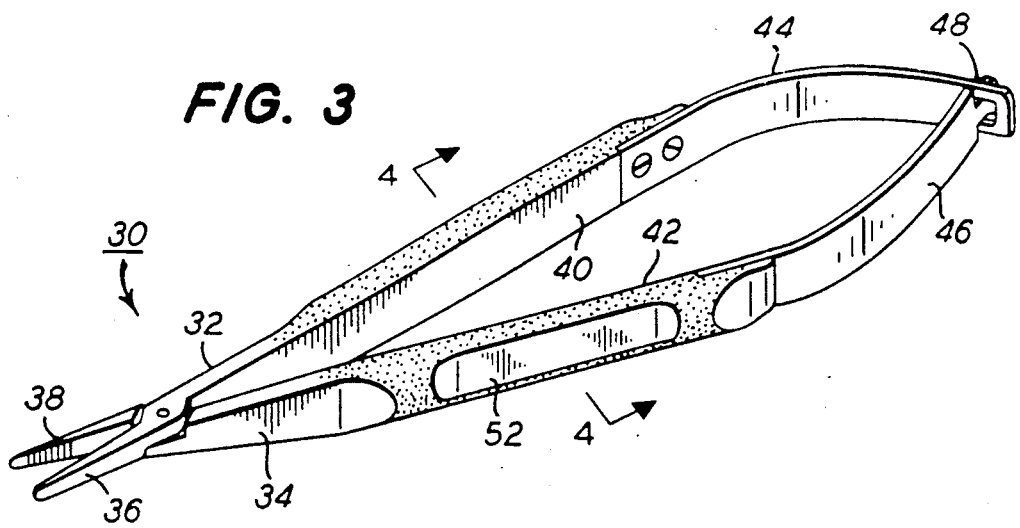
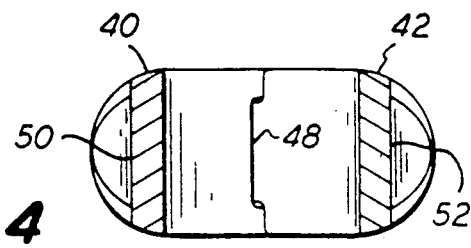

SELF ORIENTING INSTRUMENT HANDLE

This is a continuation of copending application Ser. No. 07/356,761, filed on May 24, 1989.

This invention relates in general to medical instruments and more particularly to hand held medical instruments that may be oriented to a desired position without the necessity for visually observing the instrument.

Medical instruments such as micro forceps and micro needle holders that are used to carry out delicate surgical procedures must be both precisely controllable and flexible in use. Heretofore, in order to allow the user to orient an instrument in any desired position, it has been the practice to provide the instrument with a substantially cylindrical handle that can be readily rotated in the hand to orient the tip of the instrument in the desired position. Such an instrument is very flexible to control in use and permits the user to manipulate needles or tissue easily by rotating the instrument with the fingers. However, the very structure that permits the desirable flexibility does not allow the user to determine how the instrument is oriented without looking at it. Once the tips are closed, the instrument feels the same in all positions. If the instrument is placed in the hand at other than the desired position, the user will not be aware of it until he observes it. At best this wastes time. At worst, the tip of the instrument may be obscurred during use and direct observation is then not possible.

In order to provide an instrument that can be oriented precisely without the need for direct visible observation, a flat handle is used. The flat handle allows the user to readily orient the tip of the instrument by feel alone. The most important disadvantage of the flat handle for instruments is that in order to rotate the tip of the instrument to either pick up a needle or to manipulate tissue, the user must rotate his hand if the tip is to be rotated more than a few degrees. Rotating the hand is awkward at best and may be impossible in tight situations as are often encountered during surgery.

It is an object of this invention to provide an improved hand held medical instrument having an instrument tip having a preferred orientation, and rotatable to at least one other orientation the tip being attached to an instrument handle adapted to be held in the hand of the user, the handle having at least one substantially round body portion for facilitating rotation of said instrument, and an at least generally flat reference surface on said body portion, the reference surface engagable by the hand of the user for orienting said instrument in said preferred orientation.

While the novel aspects of this invention are set forth with particularity in the appended claims, the invention itself together with further objects and advantages thereof may be more readily appreciated by reference to the following detailed description of the preferred embodiment thereof taken in conjunction with the drawing in which:

FIG. 1 is a perspective view of a pair of micro vascular forceps in accordance with this invention.

FIG. 2 is a section view taken along line 2—2 of FIG. 1.

FIG. 3 is a perspective view of a needle holder in accordance with this invention; and FIG. 4 is a section taken along line 4-4 of FIG. 3.

Referring now to FIG. 1, a pair of forceps having a handle in accordance with this invention is illustrated in a perspective view. FIG. 2 shows a section taken along line 2—2 of FIG. 1. Forceps of the type illustrated, and particularly micro forceps having extremely fine tips, are used in a wide variety of surgical operations, such as the atraumatic handling of the internal mammary artery and other delicate tissues. The forceps may be made from any suitable sterilizable material, such as stainless steel, or, where weight is important, titanium alloy. The forceps indicated generally at 10 include first and second relatively movable legs 12 and 14 respectively that are fastened together by welding or the like at one end 16. The legs include a handle portion 18 adapted to be gripped by the user and a tip 20 that preferably tapers from the handle to an end that may be pointed, have a ring or platform formed thereat, or have teeth, as is required for the particular surgical procedure in which the forceps are to be employed.

As may be seen by referring now to FIG. 2, each of the legs 12 and 14 of the forceps 10 is rounded, and preferably semi-circular in cross-section and includes a reference portion, preferably a substantially flat reference portion for allowing the user to precisely orient the forceps in hand, without the necessity for direct visual observation. Preferably, the flat reference surface 22 covers at least one third the length of the rounded portion of each leg, and has a depth, measured from the outer surface of each leg, equal to approximately one fourth the radius of the leg as measured from the inner surface thereof. It will be understood that while the foregoing dimensions are presently deemed to be preferred, a wide latitude in the extent and depth of the reference surface will nevertheless provide the advantages of this invention.

Preferably, the outer surface of the handle portion 18 of the forceps 10 is provided with a non-slip surface, such as a scored surface. The reference surface is preferably smooth to tactily distinguish it from the remainder of the handle, but may also be scored with the same or a different pattern to minimize the chance of slippage.

FIGS. 3 and 4 show a micro needle holder in accordance with this invention. The needle holder indicated generally at 30 has first and second pivotally attached portions 32 and 34, having opposable jaws 36 and 38 respectively, and reciprocally movable handles 40 and 42. Preferably, resilient members 44 and 46 extend from the ends of handles 40 and 42, to a point of engagement 48. The resilient portions adjustably maintain the needle holder with the jaws in an open configuration. The jaws may be closed by appropriate pressure on the handle portions. The handle portions themselves are configured substantially similarly to the handles of the forceps of FIG. 1. Each handle portion has a semi-circular cross-section and a reference surface 50 and 52 respectively, for allowing the user to precisely orient the needle holder and the needle held therein, without the need for direct visual observation while maintaining the ability to slightly rotate the needle holder to reposition the needle for fine suturing or the like. Preferably, the surface of the handles is provided with a non-slip surface, such as by scoring, which surface or a surface having a distinguishable tactile feel may also be applied to the reference surfaces 50 and 52.

While the invention has been decribed as it might be applied to forceps and needle holders, it has substantially wider application to any medical or other instrument that must be accurately held and oriented without direct visual observation.

Those skilled in the art will no doubt recognize that many modifications and changes may be made to the preferred embodiment of the invention described herein, without departing from the true spirit and scope thereof, which accordingly are intended to be limited solely by the appended claims.

What is claimed is:

1. An improved hand held medical instrument comprising:
   an instrument tip having a preferred orientation, and rotatable to at least one other orientation;
   an instrument handle connected to the instrument tip and adapted to be held in the hand of the user, said handle comprising at least one substantially rounded elongated gripping portion for facilitating rotation of said instrument to orient the instrument tip;
   a plurality of elongated longitudinally extending flat and curved gripping surfaces alternating in a radial direction around a circumference of the gripping portion and extending longitudinally over at least a substantial portion of the length of the gripping portion of the handle, the flat and curved gripping surfaces being engageable by the hand of the user while the instrument is held in a comfortable working position for providing a generally cylindrical gripping portion for ease of manipulation and flat locating positions within the cylindrical portions for orienting said instrument in said preferred orientation by touch alone.

2. The hand held instrument of claim 1 wherein said instrument handle comprises a substantially cylindrical major body portion having first and second cylindrical end portions and the alternating flat and curved gripping surfaces are disposed between said end portions.

3. The hand held instrument of claim 2 wherein said each of said first and second cylindrical end portions comprises about one third of the length of said instrument handle.

4. The hand held instrument of claim 1 wherein said tip comprises first and second opposed engageable portions disposed at first ends of first and second relatively moveable half round body portions respectively, said first and second body portions being resiliently coupled together at second ends thereof and biased to hold said engageable portions in spaced apart relationship, and wherein said reference surface comprises an at least substantially flat surface on each of said half round body portions.

5. The hand held instrument of claim 4 wherein each of said half round body portions comprises first and second half round end portions and said reference surface comprises a flat surface disposed between said end portions.

6. The hand held instrument of claim 5 wherein said each of said first and second cylindrical end portions comprises about one third of the length of said instrument handle.

7. Hand held medical tweezers comprising:
   first and second tweezer halves attached at one end, and resiliently biased to an at least slightly spaced apart position forming a generally wedge-shaped space between the tweezer halves;
   first and second opposed tweezer tips at ends of the tweezer halves opposite the attached together ends;
   first and second generally flat major surface portions adjacent the ends of each of the tweezer halves;
   substantially rounded gripping surfaces disposed between the substantially flat surface portions to form, when the tweezers are closed, a generally cylindrical gripping portion for facilitating rotation of the tweezers; and
   first and second elongated substantially flat reference surfaces disposed within and substantially completely bounded by each of the rounded gripping surfaces for providing a generally cylindrical gripping portion for ease of manipulation and flat locating positions within the cylindrical portion for engagement by the hand of the user for orienting the tweezers in a normal orientation by touch alone.

8. The tweezers of claim 7, in which the reference surfaces comprise substantially elongated generally oval shaped reference surfaces intermediate the ends of each tweezer section.

9. The tweezers of claim 7, in which the generally flat reference surfaces are oriented in planes substantially perpendicular to the direction of movement of the tweezer tips, as they are brought together.

10. Medical forceps comprising:
    first and second pivotally connected forceps halves each half having a first and second end, said halves resiliently biased to an at least slightly spaced apart position forming a generally V-shaped space between opposed first ends;
    first and second opposed forcep tips on the first ends;
    first and second substantially rounded gripping surfaces disposed between the second ends and the pivot to form, when the forceps are closed, a generally cylindrical gripping portion for facilitating rotation of the forceps; and
    first and second elongated substantially flat reference surfaces disposed within and substantially completely bounded by each of the rounded gripping surfaces for providing a generally cylindrical gripping portion for ease of manipulation and flat locating positions within the cylindrical portions for engagement by the hand of the user for orienting the forceps in a normal orientation by touch alone.

11. The forceps of claim 10, in which the reference surfaces comprise substantially elongated generally oval shaped reference surfaces intermediate the ends of each tweezer section.

12. The forceps of claim 10, in which the generally flat reference surfaces are oriented in planes substantially perpendicular to the direction of movement of the tweezer tips, as they are brought together.

* * * * *